(12) United States Patent
Levin et al.

(10) Patent No.: US 9,480,688 B2
(45) Date of Patent: *Nov. 1, 2016

(54) PHEROMONE COMPOSITIONS AND THEIR USE TO MODIFY BEHAVIOR IN DIFFERENT VERTEBRATE SPECIES

(71) Applicant: Sergeant's Pet Care Products, Inc., Omaha, NE (US)

(72) Inventors: Mark Levin, Omaha, NE (US); John J. McGlone, Lubbock, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/826,948

(22) Filed: Aug. 14, 2015

(65) Prior Publication Data
US 2015/0366878 A1  Dec. 24, 2015

Related U.S. Application Data

(63) Continuation-in-part of application No. 14/704,729, filed on May 5, 2015, which is a continuation of application No. 13/623,279, filed on Sep. 20, 2012, now Pat. No. 9,044,395.

(60) Provisional application No. 61/536,673, filed on Sep. 20, 2011.

(51) Int. Cl.
| | | |
|---|---|---|
| *A01N 63/02* | (2006.01) | |
| *A61K 8/63* | (2006.01) | |
| *A61K 31/568* | (2006.01) | |
| *A61K 45/06* | (2006.01) | |
| *A61K 9/12* | (2006.01) | |
| *A61K 9/00* | (2006.01) | |
| *A61K 31/565* | (2006.01) | |
| *A61K 9/06* | (2006.01) | |
| *A61K 47/06* | (2006.01) | |

(52) U.S. Cl.
CPC ............. *A61K 31/568* (2013.01); *A61K 9/008* (2013.01); *A61K 9/0043* (2013.01); *A61K 9/06* (2013.01); *A61K 9/124* (2013.01); *A61K 31/565* (2013.01); *A61K 45/06* (2013.01); *A61K 47/06* (2013.01)

(58) Field of Classification Search
None
See application file for complete search history.

(56) References Cited

U.S. PATENT DOCUMENTS

| | | |
|---|---|---|
| 5,272,134 A | 12/1993 | Berliner |
| 6,384,252 B1 | 5/2002 | Pageat |
| 9,044,395 B2 * | 6/2015 | McGlone ................. A61K 9/12 |
| 2005/0143465 A1* | 6/2005 | Pageat ................... A61K 31/20 514/560 |
| 2006/0252738 A1 | 11/2006 | Avelino |
| 2006/0269513 A1 | 11/2006 | Dodd |
| 2007/0048230 A1 | 3/2007 | Parsadayan |
| 2007/0048231 A1 | 3/2007 | Parsadayan |
| 2011/0150822 A1 | 6/2011 | Nouvel |

FOREIGN PATENT DOCUMENTS

| | | |
|---|---|---|
| CN | 101797257 | 8/2010 |
| WO | 9206675 | 4/1992 |
| WO | 2009134958 | 4/2009 |

OTHER PUBLICATIONS

McGlone, "Aerosolized 5a-androst-16-en-3-one Reduced Agonistic Behavior and Temporarily Improved Performance of Growing Pigs", Journal of Animal Science, 63:679-684, 1986.
Meredith, "Distinctive Responses in the Medial Amygdala to Same-Species and Different-Species Pheromones", The Journal of Neuroscience, 24(25), 5719-6725, 2004.
Markham Animal Clinic, "Cat Behavior Problems", Markham Animal Clinic, www.myvetonline.com/markhamac, 2008.
McGlone, "Reduction of Pig Agonistic Behavior by Androstenone", Journal of Animal Science, 66:880-884, 1988.
Crown Street Veterinary Hospital Website, "Breeding Dogs" http://www.crownvet.com/au/breeding.html.
Swaney et al., "The evolution of pheromonal communication", Behavioural Brain Research, Elsevier, Amsterdam, vol. 200, No. 2, Jun. 25, 2009, pp. 239-247.

* cited by examiner

*Primary Examiner* — Robert T Crow
*Assistant Examiner* — John P Nguyen
(74) *Attorney, Agent, or Firm* — Polsinelli PC

(57) ABSTRACT

A composition comprising Androstenone is described for the modification of undesirable or harmful stress-related behaviors or other behaviors or physiology in a variety of vertebrate species, as well as methods of using the compositions in vertebrates from a species different than the species in which the Androstenone is a naturally occurring pheromone.

15 Claims, 2 Drawing Sheets

Figure 2. % Efficacy for head-shy horses treated with Control with or without Noise or Pheromone A with or without Noise.

PHEROMONE COMPOSITIONS AND THEIR USE TO MODIFY BEHAVIOR IN DIFFERENT VERTEBRATE SPECIES

RELATED APPLICATION

This application is a continuation-in-part of U.S. patent application Ser. No. 14/704,729 filed on May 5, 2015, which is a continuation of U.S. patent application Ser. No. 13/623,279 filed on Sep. 20, 2012, which claims the benefit of U.S. Provisional Patent Application No. 61/536,673 filed on Sep. 20, 2011, the disclosures of which are hereby incorporated by reference in their entirety.

FIELD OF THE INVENTION

The present disclosure is broadly concerned with the field of animal behavior and the use of pheromones and INTEROMONEs® in compositions. More particularly, the present disclosure is concerned with the use of the pheromone Androstenone as an INTEROMONE® to produce a different behavioral or physiological effect (such as a calming or behavioral-altering effect) in a different vertebrate species from which the pheromone is produced, for example, such as in dogs, cats, snakes, birds, or horses.

BACKGROUND OF THE INVENTION

Pheromones are chemicals released by living organisms that send information to other organisms of the same species via scent. Pheromones are released in response to stress, alarm, danger, sexual fertility, and in other behavioral contexts. Pheromones, by definition and according to evolutionary theory, are species-specific, that is, they are effective in eliciting an innate response only in members of the same species.

Androstenone (also known as 5-α-androst-16-en-3-one) is a steroid found in a number of vertebrate species but is especially pronounced in the male domestic or wild pig. Androstenone acts as a pig sexual pheromone in that the sexually receptive female will seek the boar and express lordosis behavior in the presence of Androstenone or an intact male pig. Androstenone, the odor of an adult dominant male, also reduces aggressive behavior in younger pigs (McGlone, J. J. and J. L. Morrow. 1988. Reduction of pig agonistic behavior by Androstenone. J. Animal Science. 66:880-884). Androstenone is documented as a social pheromone in the pig that changes adult pig behavior and physiology within the same species.

Chemicals that provide interspecies communication are called allelochemicals. Some compounds are known to be a pheromone in one species, but have been observed to have strong behavioral effects in other species. For example, chemicals produced and released by one species that affect the behavior or physiology of another species to the benefit of the originator but not the receiver are known in the art as allomones (See Grasswitz, T. R. and G. R. Jones (2002). "Chemical Ecology". Encyclopedia of Life Sciences. John Wiley & Sons, Ltd. doi:10.1038/npg.els.0001716). The production of allomones in natural environments has been mainly observed in plant species, which utilize allomones for example to protect plants against insect herbivores.

A kairomone is another known allelochemical. It is emitted by one species and benefits another species, but does not benefit and often harms the emitter. The production of kairomones in natural environments has been mainly observed in insect species. For example, the Ponderosa Pine tree produces a terpene called myrcene when the Western pine beetle damages the tree. The emission of this chemical then lures more beetles to the tree (See Wyatt, T. D. (2003). Pheromones and Animal Behaviour: Communication by Smell and Taste, First Edition (Cambridge, UK: Cambridge University Press).

A synomone is an allelochemical produced and released by one species that benefits both the emitter and receiver. For example, plants emit odors that work to attract bees. The bees are attracted to the plants to feed and then the bees take the pollen to fertilize other plants/flowers.

Accordingly, the allelochemicals known in the art involve the observation of chemicals produced by one species having an effect on another species to the benefit and/or detriment of the emitting or receiving species. What is described is an allelochemical that affects the behavior and/or physiology of another species (i.e., the receiving species) without additionally having a beneficial or harmful effect on the emitting species and having a novel or unrelated behavioral or physiological effect on the receiving species.

For instance, while domestic dogs are known to bark as part of their normal method of communication, dogs may show excessive barking/jumping/mobbing/begging in response to external cues or due to boredom. Mobbing includes repetitive barking and jumping. Certain dogs will bark and jump in an excitable manner when they hear or see people, animals, vehicles, or machines. One theory is that excessive barking is part of the "mobbing" behavior that pack animals have when they attack a prey species (Lord et al., Barking and mobbing, Behav. Processes, 81:358-368, 2009).

Methods used in the art to stop the barking/jumping/begging syndrome in dogs have included shock collars, odor sprays, and loud noises, all of which work by startling or distracting the dog from engaging in the undesirable behavior. Dog appeasing pheromones, including synthetic compositions believed to replicate certain calming pheromones emitted by dogs, have also been used in the art to treat certain behavioral problems in dogs, but to date, have not been successful in alleviating the barking/jumping syndrome exhibited by certain dogs. Moreover, the pheromones used in the art have not been directed for use with animal species other than the species from which the pheromones are emitted.

Reducing and controlling stress experienced by an animal has very practical applications. Using horses as another example, most interactions between a horse and people begin with handling the horse's head. Whether the horse is being handled for basic husbandry such as stall cleaning, grooming, worming and health inspections or enjoying the horse as a companion by leading, riding, driving and other activities, interactions begin with haltering or otherwise gaining control over the horse's head to direct the horse's movements. Most horses accept this handling with no resistance, but some horses react poorly when people try to touch their head or ears, with behaviors associated with stress, nervousness and anxiety. They might flinch, toss their head, hold their head high and away from the handler, or even rear or try to strike the person attempting to touch their head. Usually handlers try to overcome the horse head-shy problem by training the horse using slow and measured movement, in an attempt to keep the horse relaxed and unstressed. While hoping the horse would gradually adjust to and accept the handling of its head, training horses that are very sensitive to touch can take very long and with no success guaranteed.

Additionally, weaning horses also undergo a tremendous amount of stress. Foals are ready to wean typically between four months and six months of age. However, because the mare-foal bond is extremely strong, weaning foals often experience separation anxiety in the first few days and could behave aggressively and get injured. A weaning foal will vocalize, run/trot, hit the fence (attempting to get back to its mother), and eat less immediately after weaning starts. The stress of weaning may also suppress the foals' immune system and makes the foals more vulnerable to conditions such as colds, flu, strangles and pneumonia. To handlers, weaning foals is equally dreadful at least in those early days. Different weaning techniques are used in the horse operations. Generally more gradual methods are less stressful than abrupt separation by suddenly taking the mare completely out of sight and earshot of the foal. However, even the gradual methods may still fail to control or reduce the stress level of the weaning foal as desired.

Accordingly, it would be desirable to provide methods and compositions comprising a compound known to be a pheromone in one species to positively modify animal behavioral problems in a variety of different vertebrate species. In particular, there is a need in the art for use of compositions comprising one or more INTEROMONEs®, such as Androstenone, to calm, sedate, reduce anxiety, or otherwise positively modify the behavior of a variety of vertebrate species, including the barking/jumping/begging syndrome exhibited by some dogs or to calm anxious dogs or cats or other vertebrate species.

SUMMARY OF THE INVENTION

It is an object of the present invention to provide novel methods for the modification of behavior in vertebrate species comprising compounds that have been isolated from one vertebrate species but, surprisingly, have the effect of modifying the behavior in a different vertebrate species. Specifically, certain pheromones have been identified which can be made into compositions and used as part of a method to have cross-species effects. An INTEROMONE® is any naturally secreted or synthetically produced chemical emitted as a pheromone within one species, which, when isolated and administered to a member of a different vertebrate species, elicits a change in behavior or physiology of the different species without the requirement of benefiting and/or harming the species from which the chemical is released.

The present disclosure is specifically concerned with the pheromone Androstenone and its use in various compositions as an INTEROMONE® to effect a modification of behavior in a variety of vertebrates, for example dogs, horses, cats, snakes, and birds. Androstenone is an odorous pheromone used by the domestic pig in sexual/courtship and social behaviors. It was surprising to learn through the present invention that Androstenone has powerful effects on other species, such as dogs and horses, and was observed to change dog and horse behavior, where the animal is experiencing stress due to various reasons.

The compositions of the invention may optionally include other ingredients as necessary or desired, depending on the form and intended use of the final product. Such optional ingredients can include, but are not limited to, carriers such as water, alcohols, solvents, and the like; fragrances, coloring agents, preservatives, antioxidants, and the like. Examples of the resultant product include, but are not limited to, an aerosol or a spray. Alternatively, the resultant product may be a diffuser, collar, spraying collar, foam, dip, wipe, cream, gel, ointment, lotion, or fabric garment.

Another object of the present invention is to provide a method for modifying or positively affecting the behavior of a vertebrate, the method comprising administering a pheromone composition comprising Androstenone, in an amount effective to affect the behavior of a particular vertebrate, wherein the vertebrate whose behavior is being modified is different than that from which the Androstenone is emitted as a pheromone.

Another object of the present invention is to provide for use of a formulation comprising Androstenone to positively affect the behavior (e.g. calm) in a different vertebrate species. It is both unexpected and surprising that a chemical known to be a pheromone in one species can have a strong positive behavioral or physiological effect on members of other vertebrate species since pheromones are, by definition, functional only within a particular species.

One aspect of the present invention provides a method of modifying behavior in a horse, the composition comprising between about 0.001% and about 1% (w/w) of Androstenone, or a synthetic version thereof, and between about 0.5% and 99.99% (w/w) of at least one carrier solvent, wherein the amount of Androstenone administered to the animal is between about 1.0 pg/mL to about 1.0 g/mL, and wherein the horse's head-shy, anxiety, stress, aggressiveness and feeding refusal is reduced.

Another aspect of the present invention provides a method of modifying head-shying behavior in a horse, the method comprising administering an effective amount of an aerosol composition to a horse's environment for a period of time, the aerosol composition comprising 0.1% (w/w) Androstenone, or a synthetic version thereof, and 99.9% (w/w) isopropyl alcohol, wherein the horse's anxiety, stress, and aggressiveness is reduced, and wherein the horse head-shying behavior is reduced or eliminated.

Yet another aspect of the present invention provides a method of modifying behavior in a weaning horse comprising administering an effective amount of a gel composition to the animal for a period of time, the gel composition comprising between about 0.0001% (w/w) and about 0.1% (w/w) Androstenone, or a synthetic version thereof, and an oily base, wherein the weaning horse's anxiety, stress, and aggressiveness is reduced. In some embodiments, the weaning horse's vocalization, head-shaking, trotting, running, or pacing is reduced. In some other embodiments, the weaning horse's feeding is improved.

Various objects and advantages of this use will become apparent from the following description taken in conjunction with the accompanying drawings wherein are set forth, by way of illustration and example, certain embodiments of this invention.

DETAILED DESCRIPTION OF THE INVENTION

Figure 1:
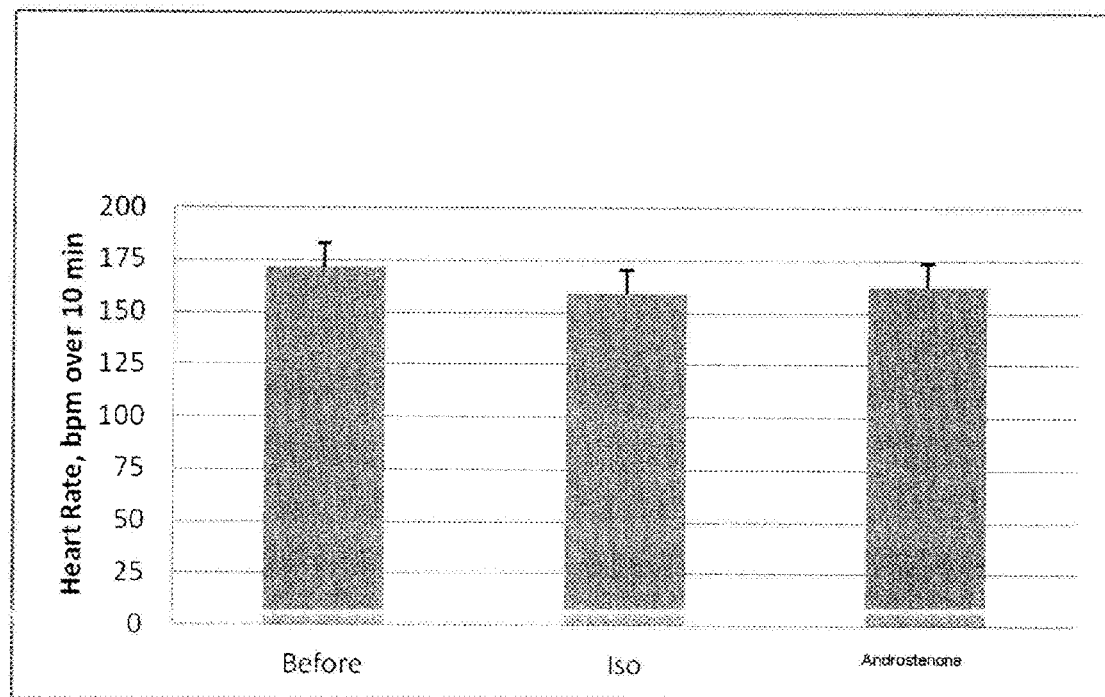
FIG. 1 is a graphic representation of a comparative test to determine whether treatment with Androstenone spray increased dogs' heart rate.

The broad term, INTEROMONE®, is used herein to refer to chemicals emitted as pheromones within one vertebrate species that influence the behavior or physiology of a different species without the requirement of benefiting and/or harming the emitter or receiving species (although an INTEROMONE® could benefit or harm the emitting or receiving species). The surprising use of specific pheromones having a cross-species effect without providing any benefit or harm to the emitting species has not heretofore been developed.

The present invention relates to the use of Androstenone in a composition as an INTEROMONE®, rather than as a pig pheromone as it is known and used in the art, in order to affect the behavior of different vertebrate species (such as, for example, dogs, cats, horses, frogs, snakes, birds, etc.). One of skill in the art will appreciate that additional pheromones not specifically disclosed herein may be found to have differential and perhaps beneficial effects in other species, such as pheromones from other mammals (e.g., cats, tigers, lions, elephants, hamsters, mice, and rats), pheromones from reptiles (e.g., snakes and lizards), pheromones from birds, or pheromones from amphibians. Androstenone has been formulated into a composition as an INTEROMONE® for administration to different species (such as, for example, the horse, dog, cat, and other vertebrates) in order to positively modify the behavior of members of the different species.

In particular, administration of Androstenone to dogs surprisingly results in reducing activity or positively modifying the behavior of dogs that exhibit the anxious behaviors.

Further, administration of Androstenone to horses surprisingly reduces head-shy behavior, and reduces stress and calms weaning foals by decreasing vocalizations, eliminating trotting, running, pacing and head shaking, and increasing feeding in the weaning foals.

The present disclosure provides for a composition comprising Androstenone, to modify the behavior of horses. When the composition comprising the Androstenone is applied to or in the vicinity of horses, the animal is calmed for a period of time. It is unexpected and surprising that a natural compound found in one vertebrate species can have a large, meaningful effect on members of another vertebrate species since pheromones are, by definition, species-specific. 2-methylbut-2-enal (as disclosed in U.S. application Ser. No. 13/623,319) and Androstenone are two examples that have been found to work in a cross-species manner. Other chemicals and their cross-species beneficial use may become apparent to those skilled in the art following the teachings of the present invention.

I. Formulations

The formulations of the present invention may comprise a chemical that is naturally secreted, isolated from a secretion, or synthetically duplicated from a vertebrate species. The chemicals that may be used in accordance with the present invention are those that produce a certain effect within the species from which they are secreted and a different effect when used in another species.

The formulations of the present invention comprise the androgen steroid known as Androstenone. The Androstenone used in the compositions may be the natural pheromone secreted or isolated directly from a male pig, or a synthesized compound characterized by the following structural formula (including enantiomers, diastereomers, or racemates thereof):

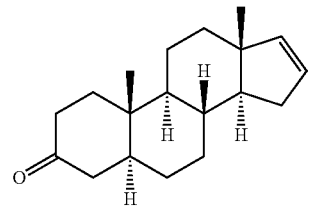

Formula I

Compounds related to Androstenone that could also be used in accordance with the present invention include, but are not limited to, androstenol, androstadienone, and estratetraenol. The amount of Androstenone in the formulation will be an amount effective to positively modify or alter the behavior (e.g., calm, reduce nervousness, or lower the heart rate) of a particular animal. Generally, the amount of Androstenone in the formulation should be at least 0.0001% (w/w) of the total composition. More particularly, the concentration of Androstenone in the composition ranges from between about 0.0001% to about 1% (w/w).

In one embodiment, the composition of the present invention contains Androstenone. In another embodiment, the composition contains a combination of Androstenone and at least one additional pheromone or pheromone composition. For instance, the composition may comprise Androstenone and at least one additional pheromone composition, such as the composition described in U.S. Publication No. 2011/0150822.

In addition to Androstenone, the formulations may optionally contain additional components such as solvents, propellants, oily bases, surface-active agents, thickeners, and/or fragrances (i.e., "additional components"). The formulation may include one additional component or a combination of any of the forgoing additional components in varying amounts. Suitable examples of each type of additional component are detailed below.

In a first embodiment, the formulation includes at least one carrier solvent. Suitable carrier solvents are generally known within the art and are recognized to include lipophilic organic diluents, alcohols, ethylene glycol, propylene glycol, dipropylene glycol, ether, chloroform, benzene, carbon disulfide, oils including non-volatile and volatile liquids and oils, water, and combinations thereof. For example, Androstenone can be dissolved in a suitable alcohol and supplied in a liquid form such as a pump spray or for use in a plug-in diffuser. Suitable alcohols include ethanol, propanol, isopropanol, butanol, pentanol, hexanol, heptanol, octanol, and phenyl ethyl alcohol. In a particular embodiment, the alcohols comprise ethanol, isopropanol, butanol, and phenyl ethyl alcohol. An alcohol solvent can be combined with water or a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In another embodiment, the solvent is a combination of water and an alcohol selected from the group consisting of ethanol or isopropanol. Generally, the amount of solvent present in the composition ranges from between about 0.5% and 99.99% (w/w) of the composition. More particularly, the amount of solvent present in the composition ranges from between about 70% and about 99.99% (w/w) of the composition or from between about 80% and about 98.5% (w/w).

The formulation may additionally include a propellant. Suitable propellants include chlorofluorocarbons (CFC)

such as trichloromonofluoromethane, dichlorodifluoromethane, and dichlorotetrafluoroethane; hydrochlorofluorocarbons (HCFC) or hydrofluorocarbons (HFC) such as chlorodifluoromethane, trifluoromonofluomethane, chlorodifluoroethane, difluoroethane, and heptafluoropropane; hydrocarbons such as propane, butane, and isobutene; and compressed gases such as nitrogen, carbon dioxide, and nitrous oxide, as well as combinations of any of the above described propellants. In one embodiment, the propellant is propane. In another embodiment, the propellant is 1,1-difluoroethane. The propellant does not comprise an inert gas of Tumorigen compound class, which includes 1,1,1,2-tetrafluoroethane, chlorodifluoromethane, and dichlorodifluoromethane. Preferably, the propellant has a flash point of less than about −50° C. Generally, when a propellant is included in the composition, the amount of propellant will range from between about 75% to about 99.99% (w/w) of the composition, preferably between about 85% and about 99.99% (w/w), and most preferably from between about 90% and about 95% (w/w).

The formulation may include an oily base. Examples of the oily base include higher alcohols such as oleyl alcohol, stearyl alcohol, cetostearyl alcohol, cetyl alcohol, benzyl alcohol and the like, fatty acid esters such as ethyl acetate, isopropyl acetate, butyl acetate, diisopropyl adipate, diethyl sebacate, isopropyl myristate, octyldodecyl oleate, octyldodecyl myristate, isostearyl myristate, lanolin and the like, medium-chain triglycerides such as beef fat, olive oil and the like, cetaceum, white petrolatum, liquid paraffin, microcrystalline wax, and the like.

The formulation may include one or more surface-active agents (also called surfactants). Surfactants are generally used in preparing those embodiments of the present invention directed to compositions that are formulated as emulsions. Either water in oil or oil in water emulsions may be formulated. Examples of suitable surfactants include: non-ionic ethoxylated and nonethoxylated surfactants, abietic acid, almond oil PEG, beeswax, butylglucoside caprate, $C_{18}$-$C_{36}$ acid glycol ester, $C_9$-$C_{15}$ alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-C12-C13 pareth-3 sulfate, tri-$C_{12}$-$C_{15}$ pareth-6 phosphate, and trideceths.

In certain applications, it may be desirable to thicken the formulation. Suitable examples of thickening or viscosity increasing agents, include agents such as acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxytheylcellulose, hydroxypropylcellulose, hydroxpropyl starch, isopropyl palmitate, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan.

The composition may additionally comprise a fragrance. The fragrance may be any fragrance that provides a desired odor masking effect since Androstenone may have a pungent odor. Although a variety of fragrances may be employed without departing from the scope of the present invention, suitable fragrances include floral essences, citrus blossoms, oil or extracts of conifers, or spices. Examples of floral essences include rose, lilac, lavender, gardenia, and jasmine. Suitable citrus blossoms include orange and lemon, and suitable oil or extracts of conifers include pine and juniper.

The composition of the present invention can be formulated using the above-mentioned components into an topical formulation II. Routes of Administration Mammals, including dogs and horses, have several anatomical organs that receive olfactory signals. The two most dominant "smell" organs are the main olfactory epithelium (MOE) and the vomeronasal organ (VNO). Other sensory fibers are in the nasal cavity that can sense odors, but the main olfactory bulb and accessory olfactory bulb (receiving signals from the VNO) are the major integrating systems.

The olfactory bulb lies at the front of the brain. It sends neuronal projections through a bone and extends these projections into the olfactory epithelium. The MOE is an extensive area with a rich blood supply and mucosa in which odor aerosol molecules pass on their way to the lungs. Odor or water droplets will settle on the MOE, and if an odor receptor is present, that odor receptor will be bound and cause activation of the sensory neurons. Among all the genes in the mammalian body, the olfactory receptors have the largest number of genes. This indicates the importance of olfactory communication in animals, some of which seems to be lost in humans.

Administration of the composition comprising an Androstenone to a subject animal is typically accomplished through any method allowing for delivery of an effective amount of the Androstenone via inhalation by the animal. Such methods of administration include, for example, placing or distributing the composition comprising the Androstenone in the environment of the animal, either by incorporating the composition into a wearable device such as a collar, or by applying (e.g. spraying or wiping) the composition to surfaces in the living environment of the animal or directly onto the animal, such as to its facial region or head. For example, the composition may be administered topically to an animal by formulating the composition containing Androstenone and one or more of the above-described additional components into an aerosol, a pump spray, a foam, a collar, a wipe, a dip, a liquid, an aqueous gel, an oily gel, an ointment, a lotion, a shampoo and/or a cream. The term "effective amount" describes an amount of Androstenone present in a composition that is sufficient to produce a noticeable modification, i.e. improvement, of animal behavior in the subject animal, as determined according to behavioral observations as described herein. The effective amount will depend on factors such as the severity of the behavior being treated; individual animal parameters including age, physical condition, size and weight; concurrent treatments; the frequency of treatment; or the mode of administration. These factors are well known to those of ordinary skill in the art and can be addressed with no more than routine experimentation.

In one embodiment, the Androstenone can be incorporated in various ways as are generally well known into a solid carrier material to form a collar or tag, and the collar or tag is then worn by the animal. The solid carrier material is selected from among those materials, typically polymeric compounds, generally recognized to be suitable for release of active compounds and set forth in further detail herein below. Alternatively, the Androstenone can be combined with a solvent to form a liquid solution and the liquid solution can be further prepared in various formulations suitable for delivery to the animal by inhalation. For example, liquid solutions can be further prepared according to methods well known in the art such as a pump spray, aerosol, foam, shampoo, dip, cream, gel, ointment, lotion, diffuser, or spot-on formulation.

In one embodiment, Androstenone is dissolved or diluted in a nonaqueous organic solvent or solvent mixture to form a solution for incorporation into a pump spray containing the Androstenone. The solution may optionally be combined with at least one additional pheromone/INTEROMONE® or pheromone/INTEROMONE® composition. An exemplary pump spray solution will comprise about 0.01% (w/w) Androstenone, about 10% (w/w) isopropyl alcohol and about 89% (w/w) water. Additionally, between about 0.5% and 1% (w/w) of a fragrance may be added to the solution.

In another embodiment, Androstenone is dissolved or diluted with a solvent and combined with a propellant to form a solution for incorporation into an aerosol spray composition containing the Androstenone. An aerosol spray solution will generally comprise about 0.01% (w/w) Androstenone, about 2% (w/w) ethanol, and about 97% (w/w) propane. Additionally, between about 0.5% and 1% (w/w) of a fragrance may be added to the solution.

In an alternative embodiment, Androstenone is dissolved or diluted with a solvent and a thickener to form a solution for use in a diffuser. The solution may optionally be combined with at least one additional pheromone/INTEROMONE® or pheromone/INTEROMONE® composition. An exemplary diffuser solution will comprise about 0.02% (w/w) Androstenone, between about 80% to about 85% (w/w) solvent, about 15% (w/w) thickener. Additionally, between about 0.25% and 1% (w/w) of a fragrance may be added to the solution.

In a further embodiment, a composition comprising Androstenone is prepared for topical administration. Such topical compositions may comprise an oily or cream base, such as to form an ointment, gel, or cream. Examples of suitable ointment and gel bases include, but are not limited to, petrolatum, petrolatum plus volatile silicones, and lanolin and water in oil emulsions. Examples of suitable cream bases include, but are not limited to, cold cream and hydrophilic ointment.

In an additional embodiment, Androstenone may be incorporated into a solid carrier material to form a matrix composition containing the Androstenone (or Androstenone combined with at least one additional pheromone/INTEROMONE® or pheromone/INTEROMONE® composition), such as a fabric garment or a collar. The matrix containing the Androstenone may be formed into a collar as is well known and amply described in the art, for example in U.S. Pat. No. 3,852,416. Typically an admixture of an active (i.e., Androstenone) and a carrier material providing the matrix is formed into strips through an extrusion process, and each strip is then formed a collar by including a fastening device such as a buckle, snap or hook. The solid carrier material forming the matrix into which the Androstenone is incorporated is for example a polymer or polymer mixture with suitable release characteristics such that the pheromone is released from the collar to be inhaled by the animal.

Suitable polymers for forming a solid substrate for making a collar are well known and include, but are not limited to, polyethylene, polyvinyl acetate, ethylene acid copolymers, ethylene acrylates, polyurethanes, styrene-butadiene, polyvinyl butyral, polyvinyl chloride (PVC), polyolefin, polyacrylate, and polymethacrylate esters, and silicon polymer. The polymers can contribute between about 50% to about 99.99% (w/w) of the collar, and typically will contribute between about 90% and about 99.99% (w/w) of the collar. Plasticizers can be incorporated into the mixture to render the polymer resin more flexible. Suitable plasticizers include phosphoric acid esters (e.g. tricresyl phosphate) or phthalic acid esters (such as dioctyl phthalate or diisodecyl phthalate (DIDP)). The collar may also include other additives such as stabilizers, for example antioxidants to protect the collar material from degradation by UV light and other oxidizing factors. Lubricants, colorants, and fillers may also be included.

Additionally, the matrix containing the Androstenone may be formed into a fabric garment as is described in the art, for example in U.S. Publication No. 2010/00319632. The Androstenone preferably contributes from between about 0.001% and about 1% (w/w), and preferably between about 0.01% and 0.5% (w/w) of the collar or fabric garment.

III. Methods of Using Androstenone to Modify Behavior in an Animal

The present invention is further directed to a method of using Androstenone compositions to positively modify undesirable or inappropriate behaviors (e.g., barking, jumping, begging, and/or mobbing) or physiology in an animal by exposing the animal to an effective amount of an Androstenone-based composition, wherein the composition comprises at least about 0.001% (w/w) of Androstenone. Generally, the composition comprises between about 0.0001% and about 1% (w/w) of Androstenone. The animal can be exposed to the composition by any method allowing inhalation by the animal over a period of time sufficient to effect a modification of the target behavior, as determined according to behavioral observations. Typically, depending on the chosen route of administration, the particular animal, and situation, the exposure of the composition to the animal will be over a period of at least one second, but can also be for a period of at least one hour, for a period between one hour and five hours, for a period of at least one day, for a period of at least one week, for a period of between one week and four weeks, for a period of at least one month, or for any period of time as may be needed to achieve a satisfactory behavioral effect. For example, an animal suffering from a temporarily induced anxiety (e.g., a trip to a veterinary office, being handled, or fireworks), may require a brief exposure to the composition before, during or after the anxiety-inducing event to relieve the anxiety and associated behavior. In contrast, an animal exposed to a stressful stimulus for a longer and continual period, such as a pet exposed to a new pet in the household, may benefit from regular exposure to the Androstenone composition for an extended period.

Commonly recognized sources of stress in animals include for example weaning, human interaction (touching to head, face, or ears), transportation (especially in motorized vehicles), boredom, lack of exercise, separation anxiety, loud noises, events that induce barking/jumping/begging or anxiety, introduction to new people or animals, and visits to a veterinary office. Animals that are stressed by exposure to such events or conditions will typically exhibit highly undesirable stress-related behavioral symptoms. Such undesirable behaviors are commonly recognized and include for example fearful behavior such as cowering or shaking; excessive chewing, barking, vocalizing (for example, noise produced from the nostrils of a horse), begging, pacing, running, trotting, pawing, or excessive laying down; hyperactivity such as jumping; aggressive behavior toward people or other animals such as growling, fighting, snappishness or biting; property destruction such as hitting or kicking the fence; and frequent urination or soiling.

The efficacy of the composition can be tested, for example, by spraying subject animals with an aerosol spray incorporating the composition, topically applying the composition to the subject animal near the animal's nose, such as with a gel or ointment composition applied with fingers to thinly coat the area under the nose of the horse, having the subject animals wear a collar incorporating the composition, or by applying the composition in the form of a liquid diffuser or the like in a physical area associated with the stress-inducing conditions for any given animal. In any case, the composition is sufficiently volatile for the animal to inhale and thus be exposed to a sufficient amount of the composition to produce a noticeable behavioral effect. For example, a reduction in undesirable outward behaviors is readily ascertainable (e.g. noticeable reduction in head-shy, aggressive displays, barking, vocalizing, and/or jumping or trotting) and, in some cases, can be supplemented by observing other physical indicators of stress such heart rate, weight changes, and secretion of stress hormones such as cortisol. When undesirable behaviors are observed, the composition of the present invention may be used to induce a temporary state of lower activity, calm and reduced excitability.

In use, the composition comprising Androstenone can be implemented in a number of different ways depending in part on the targeted animals and behavior desired to be modified. A liquid solution containing Androstenone can simply be applied directly to the coat or skin of the animal, or sprayed on surfaces or objects in the animal's environment, or diffused or sprayed into the air in the animal's environment. For example, an exemplary liquid spray formulation containing Androstenone (dissolved in a suitable solvent) can be sprayed, for example, on the animal's nostrils, face, or head, or in its environment such that it may be perceived through olfaction as frequently as needed to obtain the desired behavioral modification. Alternatively, Androstenone in liquid, gas, or solid form can be incorporated in a plasticized material such as PVC or the like that can then be formed into a tag, or in strips to form a collar. In addition, Androstenone in a form of gel or ointment, may be wiped in the nostrils of the animal. Furthermore, the composition may be combined with at least one additional pheromone/INTEROMONE® or pheromone/INTEROMONE® composition (natural or synthetic) prior to implementation into any of the above-mentioned modes of delivery to the animal.

It should be understood that the Androstenone used in the composition may be provided in the form of pure concentrate (100% concentration) or a diluted composition with additional excipients in the dosage form (i.e. the amount of active ingredient in the composition is less than or equal to 99.99%, and the remainder consists of inactive excipients). If diluted, the amount of Androstenone dispensed in the various dosage forms may range from between about 1.0 pg/mL to about 1.0 g/mL, more preferably between 1.0 pg/mL to about 1.0 mg/mL, or from 1.0 mg/mL to 1.0 g/mL, and even more preferably between about 1.0 ng/mL to about 1.0 g/mL. One of skill in the art will appreciate that the volume of active component added to the composition will need to be adjusted to account for the dilution and to ensure the end composition comprises the appropriate final concentration of Androstenone. One of skill in the art will also appreciate that the various components of the composition may be provided in a variety of dosage forms including, but not limited to liquid solution or suspension, emulsion, aerosol, slow release matrices, and the like.

The compositions according to this invention may be applied in a variety of ways but are best applied by exposing the olfactory system by any means such as, for example, spraying a light mist directly on the facial region or in the environment of the animal whose behavior is intended to be modified. Further, the methods of the current invention are best accomplished by allowing the animal to inhale the composition, as the nasal cavities, sinuses, lungs and throats of animals present a large area for the aromatic molecules to be bound to an olfactory receptor. The application of the composition to the animal or the animal's environment may be repeated as often as necessary to modify the animal's behavior.

In certain aspects, the composition comprising Androstenone may be administered to horses that are head-shy, meaning that they are sensitive to a trainer's or a handler's touch to their heads, ears or faces. The composition comprising Androstenone may be administered to the head shy horse using aerosol spray with or without a noise-making device. The composition can be re-sprayed as often as needed to reduce or control head shy behavior in the horse as long as such behavior change is desired. The effects of the Androstenone spray composition on the head shy horse may last from about 15 minutes to about an hour, depending on the animal and the degree of head shy behavior to be minimized or eliminated.

In certain aspects, the Androstenone composition may be administered to a weaning foal in order to reduce or control its stress and separation anxiety from the weaning process. The Androstenone composition may be administered to a weaning foal in an ointment or gel form. In another embodiment, the Androstenone composition may be administered to a weaning foal in an ointment form. In certain embodiments, the Androstenone composition may be administered by wiping or spreading an effective amount of the composition to the nose, under the nose, or in one or both nostrils of the weaning foal using fingers or an applicator. In certain embodiments, a thin layer of the composition is all that is required to be applied, but, depending on the animal and the degree of behavior issues, more may be applied until the desired behavior changes are observed in the animal. Following administering the Androstenone composition to a weaning foal, the stress-associated behavior of the foal was found be reduced for a period of at least about 20 minutes, preferably for a period of at least about 30 minutes, more preferably for a period of at least about 60 minutes, and most preferably for a period of at least about 90 minutes. The composition can be reapplied as often as needed to reduce or control stress and separation anxiety in the weaning foal as long as such behavior change is desired. The effects of the Androstenone ointment or gel on the weaning foal may last from about 30 minutes to about 90 minutes, depending on the animal and the degree of stress or separation anxiety to be minimized or eliminated.

In certain embodiments, the vocalization of the weaning foal is reduced by at least about 40%, preferably by at least about 50%, and more preferably by at least about 60%, following administration of Androstenone composition, when compared to the weaning foals not given the same composition (control). In certain embodiments, the behavior associated with stress and anxiety during the weaning period (e.g., trotting, running, pacing, and head shaking), is reduced by at least about 70%, preferably by at least about 80%, more preferably by at least about 90%, and even more preferably by about 100%, following administering of the Androstenone composition, when compared to the control. A reduction by about 100% means that the excessive trotting, running, pacing, or head shaking due to separation anxiety and stress during weaning is completely eliminated. In certain embodiments, the weaning foal's feeding increases by at least about 60%, preferably by at least about 70%, preferably by at least about 80%, more preferably by at least about 90%, and even more preferably by about 98%, when compared to the control.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

As used herein, "a" and "an" mean one or more, unless otherwise indicated.

As used herein, "INTEROMONE®" means any naturally secreted or synthetically produced chemical released by one species, which, when administered to a member of a different vertebrate species, elicits a change in behavior or physiology of the different species with or without providing a benefit or harm to the species from which the chemical is released.

As used herein, "vertebrate" or "vertebrate species" is interchangeable with the word "animal" or "animal species" and encompasses any group of animals distinguished by possession of a vertebral column. Examples of vertebrate species include, but are not limited to, domestic animals such as cats and dogs; small animals, such as hamsters, rabbits, ferrets, rats, mice, and guinea pigs; commercial animals, such as horses, sheep, cattle, and swine; animals in captivity, such as apes, chimpanzees, tigers, lions, bears, elephants, zebras; amphibians such as frogs and salamanders; reptiles such as snakes, turtles, crocodiles, alligators, and lizards; birds, and the like.

Although the invention described herein is susceptible to various modifications and alternative iterations, specific embodiments thereof have been described in greater detail above. It should be understood, however, that the detailed description of the use of Androstenone is not intended to limit the invention to the specific embodiments disclosed. Rather, it should be understood that the invention is intended to cover all modifications, equivalents, and alternatives falling within the spirit and scope of the invention as defined by the claim language.

EXAMPLES

Example 1

Preparation of Aerosol Spray Composition Containing Androstenone for Use on Dogs An aerosol composition comprising Androstenone was prepared in accordance with the formulation set forth in Table 1.

TABLE 1

| Aerosol Spray with Androstenone | | |
|---|---|---|
| Ingredient | % | grams |
| Androstenone | 0.01 | 0.01 |
| Ethanol | 2.00 | 2.00 |
| Propane (propellant) | 97.99 | 97.99 |
| Total | 100.00% | 100 |

Example 2

Determining the Efficacy of an Aerosol Spray Composition Containing Androstenone to Modify Behavior of Dogs An aerosol spray composition comprising Androstenone solution was prepared in accordance with Example 1, but was then diluted in isopropyl alcohol to obtain a 1:1,000 dilution of the original concentration. The purpose of the dilution was to mask the odor of the Androstenone, which can be smelled by humans at high concentrations. The spray solution was placed in a metal aerosol can pressurized with propane. A noise making device was also added to the aerosol can. The propellant, when forced through small holes, caused a sound that exceeded 70 decibels.

The efficacy of an aerosol spray composition containing Androstenone was tested in a commercial research facility housing a large number of dogs. A designated person walked the aisles of the kennel with a calm dog on a leash in order to identify those dogs that met the criteria of barking/jumping. The calm dog on the leash was walked in the center aisle between kennels and also sat outside the kennels. To qualify as a test subject, a dog had to repeatedly jump and bark while the calm dot and the person were in the aisle. A total of 15 dogs were chosen as test subjects.

The dogs were separated into two treatment groups. The dogs in treatment group #1 were the control group and were only treated, when observed to be engaging in barking/jumping behavior, with a loud spray that did not contain any Androstenone. The dogs in treatment group #2 were treated, when observed to be engaging in barking/jumping behavior, with a loud spray canister to which the diluted spray composition containing Androstenone had been added. The test period was for 1 minute. Dog barking/jumping was considered "stopped" if the dog did not bark or jump for at least 60 seconds after treatment was administered. In some cases, if the control (placebo) spray did not stop the barking/jumping in a particular dog or it resumed within 60 seconds following the initial treatment, then the dog was treated with the loud spray plus Androstenone.

Table 2 sets forth the treatments and findings with regard to efficacy. When the loud spray alone (placebo) was applied directly in the facial/snout region of the barking/jumping dogs, 44% of the dogs stopped barking and jumping for at least one minute. When the loud spray plus Androstenone was applied directly in the facial/snout region of the barking/jumping dogs, 100% of the dogs stopped barking/jumping for more than one minute and did not resume barking while the evaluators were present.

The dogs in treatment group #1 that did not initially respond to the placebo were re-sprayed with the Androstenone spray. Of these dogs, the re-spray with Androstenone resulted in 83.5% of the dogs remaining calm and not barking/jumping. Twelve dogs in total received the Androstenone spray and 11 dogs were calmer and did not bark or jump after treatment with the test spray, which resulted in an overall efficacy rate of 91.7%. The one dog that did not respond based on this criterion did stop barking/jumping for 40 seconds, but then, although calmer, resumed barking 40 seconds after the Androstenone spray was applied.

TABLE 2

Results of Androstenone Spray Treatment Tests

| Group | Treatment Administered | Number of Dogs in Group | % Effective (no barking/jumping within 1 minute) |
|---|---|---|---|
| 1 | Loud spray only (placebo) | 9 | 44.4% |
| 2 | Loud spray plus Androstenone | 6 | 100% |
| 3 | Placebo first, then Androstenone spray | 6 | 83.5% |
| — | Overall Androstenone efficacy | 11 | 91.7% |

The diluted Androstenone was observed to cause an immediate cessation of barking/jumping in dogs and was also observed to make dogs calmer, even appear mildly sedated making them more cooperative to handlers. The results of this test indicated that using Androstenone in a spray on dogs is a useful training tool because the composition containing the INTEROMONE® reduced dog excitability in a safe, humane manner.

Example 3

Determination of the Effects on Heart Rate from Application of Androstenone to Anxious Dogs A study was conducted to determine whether dogs' heart rate increased following application with an aerosol spray containing Androstenone.

An aerosol spray was prepared which contained about 0.1 µg/mL of Androstenone and isopropyl alcohol using the formulation provided in Example 1.

Four dogs determined to be "anxious" were fit with telemetry jackets and transmitters in order to continually monitor heart rate. Dot heart rates were measured for 10 minutes before treatment, 10 minutes following treatment with a control spray (isopropyl alcohol only), and 10 minutes following treatment with the test spray containing Androstenone and isopropyl alcohol.

FIG. 1 illustrates the data obtained on heart rate. The graph sets forth that both the control spray and the Androstenone spray had no significant effect on the heart rate of the dogs.

Example 4

Preparation of a Pump Spray Containing Androstenone and Use on Dogs and Horses

A pump spray formulation containing Androstenone can be prepared according to typical industry techniques described above. Table 3 is the list of ingredients that can be used to prepare a liquid spray formulation comprising Androstenone.

TABLE 3

Pump Spray Formulation with Androstenone

| Ingredient | % | grams |
|---|---|---|
| Androstenone | 0.01 | 0.01 |
| Isopropyl Alcohol | 10.00 | 10.00 |
| Lavender Chamomile frag. #AA101592 | 0.50 | 0.50 |
| D.I. water | 89.49 | 89.49 |
| Total | 100.00% | 100.00 |

The resultant spray formulation, when sprayed onto the facial/snout region or in the environment of a dog or horse, will cause the animal to exhibit a significant change in behavior towards a calmer demeanor.

Example 5

Preparation of Aerosol Spray Composition Containing Androstenone for Use on Horses An aerosol spray composition comprising Androstenone was prepared in accordance with the formulation set forth in Table 4.

TABLE 4

Androstenone Spray Formulation

| Ingredient | % | grams |
|---|---|---|
| Androstenone Concentrate | | |
| Androstenone | 0.10 | 0.10 |
| Ethanol | 96.66 | 96.66 |
| Lavender Sach | 3.34 | 3.34 |
| Total | 100.00% | 100.00 |
| Aerosol Spray | | |
| Androstenone Concentrate | 6.00% | 6.00 |
| Propellant | 94.00% | 94.00 |
| Total | 100.00% | 100.00 |

Example 6

Determining the Efficacy of an Aerosol Spray Composition Containing Androstenone to Modify Behavior of Head Shy Horses An aerosol spray composition made in accordance with Table 4 was prepared for administering to adult horses that were observed to be head shy. The spray solution was placed in a pressurized metal aerosol can. In one group of aerosol cans, a noise making device was also added to the aerosol can. The propellant, when forced through small holes upon pressing the nozzle, caused a sound that exceeded 70 decibels. In a second group of aerosol cans, the noise making device was not added to the can, such that when the spray composition was pumped, no noise was made.

The efficacy of an aerosol spray composition containing Androstenone was tested using thirteen adult horses, all of which were enrolled in this study after being evaluated and categorized as head shy and hard to handle (i.e., observed to move their heads away from the handler when the handler attempted to touch their heads with his hand or a halter).

The thirteen horses were sorted into two treatment groups. One group (Group 1) of 10 horses received the Androstenone spray composition outlined in Table 4 and control (CON isopropyl alcohol) with noise (n=10), while the second group (Group 2) received the Androstenone spray and control without noise (n=3).

In each group, the control composition was administered to the horses first and then the Androstenone spray was administered to the horses the following day immediately before the handler attempted to touch their ears and heads. The horses' behavior was then recorded and evaluated after each administration. The horses were given a numerical score of 1 through 5. A score of 1 meant the treatment had little to no effect on the head-shy behavior, while a score of 5 indicated that the horse was significantly impacted and became easier to handle.

Figure 2:
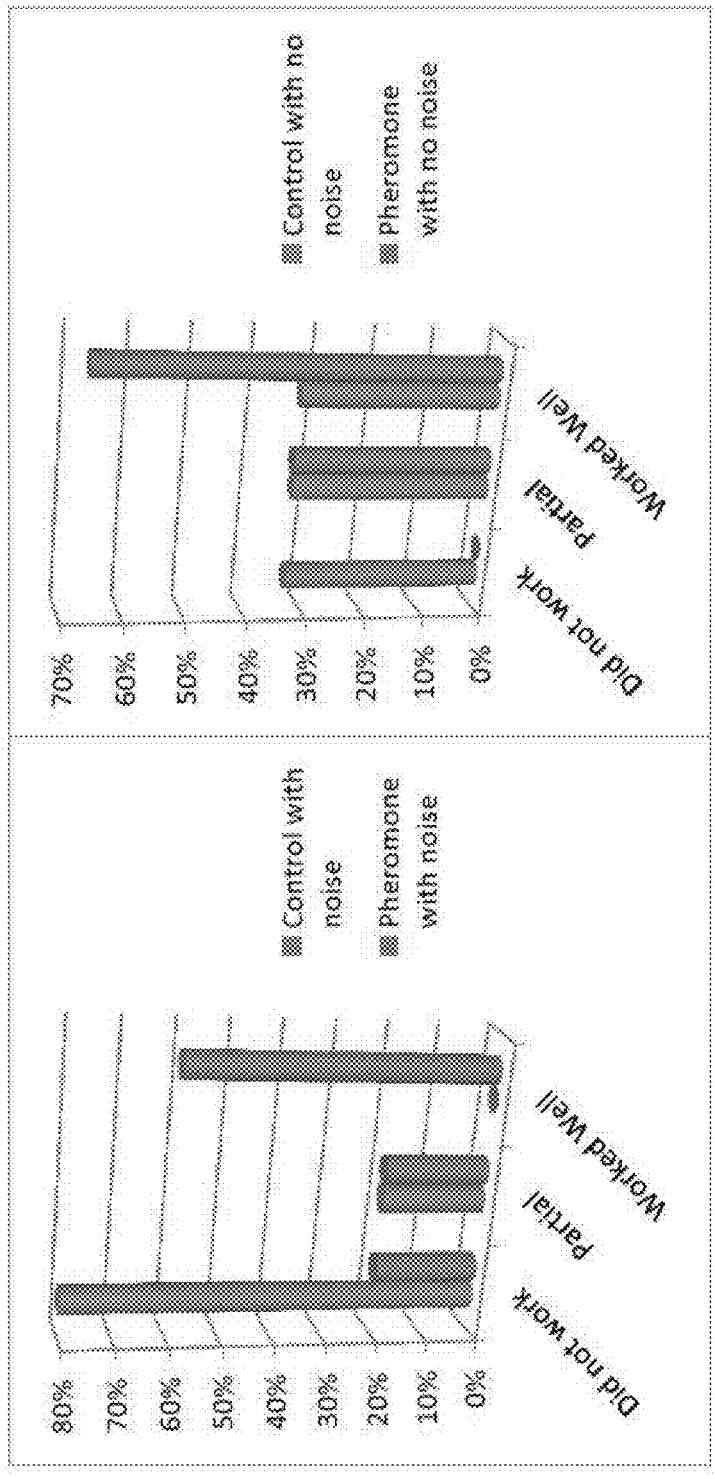
FIG. 2 is a graphic representation showing efficacy for head-shy horses treated with control with or without noise when spraying, or Androstenone with or without noise when spraying.

Horses from Group 1 were observed to be responsive to both the control and the Androstenone spray with noise as shown below in Table 5. The results were categorized as three groups in order to depict the effect of the treatment: Did not work; Partially worked; and Worked well. The control with noise partially improved head shy behavior in 20% of the horses (n=2) and did not work in improving head shy behavior in 80% of the horses. In comparison, the Androstenone composition with noise worked well for 60% of the horses and partially worked for 20% of the horses (total 80% or 8 horses). The Androstenone composition with noise did not work for 20% of the horse treated. FIG. 2 depicts in graphic form the results outlined in Table 5.

TABLE 5

Average Scores and % Efficacy for Group 1 Treatment:

| Group 1 - Treatment | | N | Avg. Score | Did not work | Partially worked | Worked well |
|---|---|---|---|---|---|---|
| Control | with noise | 10 | 1.6 | 80% | 20% | 0% |
| Pheromone | with noise | 10 | 3.9 | 20% | 20% | 60% | t = 5.799,
P < 0.01,
SE = 0.397

Horses from Group 2 were observed to have similar results compared to Group 1. The percent efficacy for the control and Androstenone composition can be seen in Table 6. The sample size was very small for this group. The control treatment did not change the horse behavior much, as one horse was identified in each category (Did not work, Partially worked, and Worked well). The results in Table 6 demonstrate the placebo effect from the non-noise control spray, which was observed to resolve behavioral issues with some head-shy horses (2 of the 3 horses treated with the no noise control spray). However, the Androstenone composition with no noise spray worked partially with one horse (33%) and worked well with 2 horses (66%). As such, 100% of horses in Group 2 had some or total improvement in behavior with Androstenone administered in a spray without noise.

TABLE 6

Average Scores and % Efficacy for Group 2 Treatment:

| Group 2 - Treatment | | N | Avg. Score | Did not work | Partially worked | Worked well |
|---|---|---|---|---|---|---|
| Control | No noise | 3 | 1.6 | 33% | 33% | 33% |
| Pheromone | No noise | 3 | 3.9 | 0% | 33% | 67% | t = 2.24,
P < 0.01,
SE = 0.745

FIG. 2 depicts in graphic form the results shown in Table 5 and Table 6, which provides comparison between Androstenone spray composition with and without noise in view of the control spray with and without noise. The Androstenone composition sprayed without noise was found to work better at reducing head shy behavior in horses, compared to the Androstenone spray composition with noise: with noise, 80% of horses showed improvement, either fully or partially, in head shy behavior; without noise, 100% of horses showed improvement, either fully or partially, in head shy behavior. Therefore, the use of an Androstenone spray composition without startling noise was most effective in reducing head-shy behavior of horses during handling.

Example 7

Determining the Efficacy of an Ointment Composition Containing Androstenone to Modify Behavior of Horses Under Weaning Stress Weaning is stressful for horses. Weaned colts will vocalize, run/trot, hit an electric fence (attempting to get back to its mother), and eat less immediately after weaning.

A total of 20 foals divided into two groups (Group A, n=10; Group B, n=10) were weaned in pens of similar size and at the same time of the day (9 am), and were evaluated using a control and pheromone compositions. All horses were between 5 and 6 months of age and mixed breeds, primarily quarter horses. An ointment form of the composition comprising Androstenone was prepared in accordance with Table 7 for administering to the horses in this study.

TABLE 7

Ointment Formulation with Androstenone

| Ingredient | % | grams |
|---|---|---|
| Blond Petrolatum | 87.9999 | 87.9999 |
| Lanolin, USP, Extra Deodorized | 10.0000 | 10.0000 |
| Cetyl Alcohol | 2.0000 | 2.0000 |
| Androstenone | 0.0001 | 0.0001 |
| Total | 100.0000% | 100.0000 |

An ointment composition containing a different pheromone, 2-methylbut-2-enal (RP, 1 mg/mL), was also prepared for administration in a comparison study. An ointment containing no pheromone was prepared and used as control (CON). In group A, 5 foals were used for the control treatment, 3 foals were used for the RP treatment, and 2 foals were used for the Androstenone treatment. In group B, 3 foals were used for the control treatment, 3 foals were used for the RP treatment, and 4 foals were used for the Androstenone treatment. As such, a total of 8 foals were used for the control treatment, 6 foals were used for the RP treatment, and 6 foals were used for the Androstenone treatment in this entire study. Both of the pheromone formulations and the control were applied to each nostril. Control treatments were administered first to prevent any cross contamination to horses during day two.

Behavioral observations were taken during the first 10 minutes (Group A and Group B) and then for four hours (Group B only) after the mares were separated from their foals. Foal behavior was recorded every minute during the first hour (or 10 minutes) and every 5 minutes for the remaining 3 hours of the study for Group B.

Table 8 provides the definitions of behaviors recorded during the weaned foal study. Behaviors were not mutually exclusive.

TABLE 8

Behavior Definitions

| | |
|---|---|
| Pace | Walking in a repeated pattern |
| Fight | The biting, pawing, and kicking directed at another horse |
| Paw | Hoof scraping or scratching the ground |
| Trot | The gait between a walk and a canter, in which diagonal pairs of legs move forward together |
| Head Shake | Shaking of the head |
| Lying | Horse's body not supported by any limb. |
| Feeding | Head in feeder/trough |
| Defecate | Defecation observed |
| Standing | Supported by limbs, not moving/walking/pacing |
| Walking | Locomotion in any pattern but not repeating |
| Interacting | Touching of another horse in any way except fighting |
| Drink | Head in water trough |
| Shock | Shocked by electric fence running along the outside of each pen |
| Vocal | Noise produced from the nostrils of the horse |

The number of shocks received by the electric fence (as foals tried to return to their mare) and vocalizations were recorded continuously. The total number of observations of each defined behaviors over the first 4 hours in Group B is presented in Table 9, which also provides the percentage of each behavior over the total number of recorded number of behaviors.

TABLE 9

Number of observations for each behavior and the percentage of each behavior under different treatments in Group B (n = 10)

| | Total observations | | | Percent of observations | | |
|---|---|---|---|---|---|---|
| BEHAVIOR | CON | RP | Pheromone A | CON | RP | Pheromone A |
| Number foals | 5 | 3 | 2 | | | |
| pace | 3 | 10 | 0 | 0.5 | 1.4 | 0.0 |
| fight | 0 | 0 | 0 | 0.0 | 0.0 | 0.0 |
| paw | 4 | 0 | 0 | 0.7 | 0.0 | 0.0 |
| trot | 29 | 22 | 0 | 4.8 | 3.1 | 0.0 |
| head shake | 7 | 1 | 0 | 1.2 | 0.1 | 0.0 |
| lying | 5 | 0 | 0 | 0.8 | 0.0 | 0.0 |
| feeding | 34 | 21 | 27 | 5.7 | 2.9 | 11.3 |
| defecation | 1 | 2 | 0 | 0.2 | 0.3 | 0.0 |
| stand | 339 | 220 | 141 | 56.5 | 30.8 | 58.8 |
| walk | 38 | 10 | 22 | 6.3 | 1.4 | 9.2 |
| interact | 19 | 0 | 2 | 3.2 | 0.0 | 0.8 |
| drink | 3 | 2 | 0 | 0.5 | 0.3 | 0.0 |
| shock | 4 | 7 | 2 | 0.7 | 1.0 | 0.8 |
| vocal | 114 | 422 | 46 | 18.8 | 58.6 | 19.0 |
| Total | 605 | 720 | 242 | | | |

As shown in Table 9, the three treatments, Androstenone, RP and control, had different effects on behavior. In particular, trotting, eating, standing, walking, and total vocalizations in foals treated with pheromone (Androstenone or RP) were all significantly changed compared to the control (CON) treatment. The trotting percent was highest in the control treatment (4.3%), followed by RP (3.1%), and then Androstenone (0%). Trotting is a sign of stress and excitement. The higher the number or percentage of the trotting, the more the horse is stressed or excited. The data showed that administering Androstenone eliminated the trotting behavior, which indicates an effective stress reduction.

In addition, horses under the control treatment vocalized 114 times, while RP-treated horses increased vocalizations 372% (from 114 to 422) more than those under control treatment, which was not a desirable outcome. However, this study showed that different pheromones have different effects on specific behaviors. As to vocalization, Androstenone was found to reduce vocalizations 60% (from 114 to 46)—a striking effect in comparison to the rabbit pheromone (2-methylbut-2-enal).

In addition, feeding (eating hay) decreased with the administration of RP, while Androstenone was found to increase feeding behavior by 98%.

Overall, the rabbit pheromone (RP) was found to make the increase or worsen stress of weaning foals. While they vocalized much more than the control foals, there was largely no difference in behavior as between the control and RP-treated foals. Clearly, Androstenone reduced excitability (trotting), stress vocalizations and increased feeding behaviors. These are all signs that Androstenone effectively reduced stress in weaning foals.

The behavior observations in the first 10 minutes post-weaning in both Group A and Group B were analyzed, and the results are shown in Table 10:

TABLE 10

Observations in the first 10 minutes post weaning under different treatments (n = 20)

| | Total observations | | | Percent of observations | | |
|---|---|---|---|---|---|---|
| Behavior | CON | RP | Androstenone | CON | RP | Androstenone |
| Number foals | 8 | 6 | 6 | | | |
| pace | 2 | 2 | 0 | 3.6 | 6.1 | 0.0 |
| fight | 0 | 0 | 0 | 0.0 | 0.0 | 0.0 |
| paw | 0 | 0 | 0 | 0.0 | 0.0 | 0.0 |
| trot | 13 | 22 | 0 | 23.6 | 66.7 | 0.0 |
| head shake | 6 | 0 | 0 | 10.9 | 0.0 | 0.0 |
| lying | 0 | 0 | 0 | 0.0 | 0.0 | 0.0 |
| eat | 0 | 0 | 0 | 0.0 | 0.0 | 0.0 |
| defecation | 1 | 0 | 0 | 1.8 | 0.0 | 0.0 |
| stand | 25 | 8 | 18 | 45.5 | 24.2 | 81.8 |
| walk | 6 | 1 | 4 | 10.9 | 3.0 | 18.2 |
| interact | 2 | 0 | 0 | 3.6 | 0.0 | 0.0 |
| drink | 0 | 0 | 0 | 0.0 | 0.0 | 0.0 |
| shock | 1 | 4 | 0 | 1.7 | 3.3 | 0.0 |
| vocal | 2 | 85 | 13 | 3.4 | 69.7 | 37.1 |
| Total | 58 | 122 | 35 | | | |

As shown in Table 10, behaviors such as pacing, trotting, head shaking, standing, walking, interacting, and total vocalizations were all changed by at least one pheromone compared to the control treatment as soon as during the first 10 minutes after weaning. In particular, horses treated with RP increased trotting and horses treated with Androstenone decreased trotting compared to horses treated with control. The total number of vocalizations was also changed as horses treated with RP vocalized 85 times (a 42-fold increased over controls). Horses treated with Androstenone vocalized 13 times, compared to the horses treated with control which vocalized only 2 times during the first 10 minutes after weaning.

In summary, RP caused weaned foals to increase head shaking, pacing and vocalizations even in the first 10 minutes after weaning. In contrast, Androstenone began to cause some positive behavioral effects as early as in the first 10 minutes. Androstenone reduced pacing, trotting, and head shaking. Vocalizations were not reduced by Androstenone during the first 10 minutes but the reduction up to 60% was observed during the 4-hour period. It was not clear how long it would take for Androstenone to start reducing vocalizations, but it was clear that its effects on vocalizations required longer than 10 minutes. However, the effect of Androstenone in reducing excitability was shown to appear as soon as in the first 10 minutes, for example, pacing, trotting, and head shaking, whereas some other behavior(s) change took longer to demonstrate, but not longer than 4 hours, with vocalization being one of the example. Combining the results from the 10-minutes and the 4-hour observations, it was concluded that Androstenone, but not rabbit pheromone, is effective in reducing stress in weaned foals.

Overall, compared with control ointment, Androstenone in ointment form reduced foal vocalizations 60%, eliminated trotting/running (100% reduction), reduced pacing 100%, reduced head shaking 100%, and increased feeding 98% (nearly doubled % of observations eating hay) over the 4 hour period after weaning. Androstenone in ointment form thus induced calm and reduced stress as indicated by behavioral signs in weaned foals. In contrast, other maternal pheromones, such as 2-methylbut-2-enal, which may remind the foal of its mother's smell, caused more behavioral problems in weaned foals.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of modifying behavior in a horse comprising: administering a pheromone composition to the horse as needed for a period of time, the composition comprising between about 0.001% and about 1% (w/w) of Androstenone, or a synthetic version thereof, and between about 0.5% and 99.99% (w/w) of at least one carrier solvent, wherein the amount of Androstenone administered to the horse is between about 1.0 pg/mL to about 1.0 g/mL, and wherein head shy behavior in the horse is reduced.

2. The method of claim 1, wherein the method of administration is inhalation.

3. The method of claim 1, wherein the composition further comprises a propellant.

4. The method of claim 1, wherein the composition is formulated as a spray, an aerosol, a diffuser, or a slow release matrix.

5. The method of claim 4, wherein administering the spray composition and the aerosol composition comprises spraying the horse or spraying the horse's environment with the composition.

6. The method of claim 1, wherein the composition comprises at least one additional pheromone or pheromone composition.

7. The method of claim 1, wherein the period of time is at least one second.

8. The method of claim 1, wherein the period of time is at least one week.

9. The method of claim 1, wherein the period of time is at least one month.

10. A method of modifying behavior in a horse comprising: administering an effective amount of a pheromone composition to the horse as needed for a period of time, the composition comprising between about 0.0001% and about 1% (w/w) Androstenone, or a synthetic version thereof, wherein anxiety, vocalization, and stress associated with weaning of the horse is reduced.

11. The method of claim 10, wherein the composition is formulated as a gel, an ointment, or a cream.

12. The method of claim 10, wherein administering the composition comprises topically applying an effective amount of the composition to the horse's nose, beneath the horse's nose, inside at least one of the horse's nostrils, or on the horse's body.

13. The method of claim 10, wherein head-shaking, trotting, running, or pacing associated with weaning of the horse is reduced.

14. The method of claim 10, wherein the feeding by the horse is increased.

15. The method of claim 11, wherein the ointment composition comprises about 0.0001% (w/w) Androstenone, or a synthetic version thereof, about 87.9999% (w/w) petrolatum, about 10% (w/w) lanolin, and about 2% (w/w) cetyl alcohol.

* * * * *